United States Patent
Lee et al.

(10) Patent No.: US 8,202,548 B2
(45) Date of Patent: *Jun. 19, 2012

(54) CHLORINE DIOXIDE GEL AND ASSOCIATED METHODS

(75) Inventors: Sunggyu Lee, Columbia, MO (US); Patricia Roberts, Columbia, MO (US)

(73) Assignee: Dharma IP, LLC, Charlottesville, VA (US)

( * ) Notice: Subject to any disclaimer, the term of this patent is extended or adjusted under 35 U.S.C. 154(b) by 1182 days.

This patent is subject to a terminal disclaimer.

(21) Appl. No.: 11/879,920

(22) Filed: Jul. 19, 2007

(65) Prior Publication Data

US 2008/0181973 A1    Jul. 31, 2008

Related U.S. Application Data

(60) Continuation of application No. 11/803,518, filed on May 15, 2007, now Pat. No. 8,088,417, which is a division of application No. 10/682,728, filed on Oct. 9, 2003, now Pat. No. 7,229,647.

(51) Int. Cl.
*A01N 59/00* (2006.01)
*A01N 25/02* (2006.01)
*A01N 25/04* (2006.01)
*A01N 25/08* (2006.01)
*A01N 25/22* (2006.01)
*A61L 2/16* (2006.01)
*A61L 2/23* (2006.01)

(52) U.S. Cl. ........ 424/661; 424/405; 424/484; 424/486; 424/487; 514/772.2; 514/772.3; 514/944; 514/970; 422/37

(58) Field of Classification Search .............. 424/405, 424/487, 661, 484, 486; 514/772.2, 772.3, 514/944, 970

See application file for complete search history.

(56) References Cited

U.S. PATENT DOCUMENTS

| | | | |
|---|---|---|---|
| 4,861,514 A | 8/1989 | Hutchings | |
| 4,891,216 A | 1/1990 | Kross | |
| 5,360,574 A | 11/1994 | Iwahashi | |
| 5,651,996 A | 7/1997 | Roozdar | |
| 5,855,861 A | 1/1999 | Lee | |
| 6,039,934 A | 3/2000 | Alliger | |
| 6,051,135 A | 4/2000 | Lee | |
| 6,379,685 B1 | 4/2002 | Richter | |
| 6,451,253 B1 | 9/2002 | Pitochelli | |
| 7,229,647 B2 * | 6/2007 | Lee et al. ................. 424/661 |
| 2005/0079230 A1 * | 4/2005 | Lee et al. ................. 424/661 |

OTHER PUBLICATIONS

Kirk-Othmer, Encyclopedia of Chemical Technology, John Wiley & Sons, New York, 4th ed., vol. 5, 1993, pp. 969-970; 989-991.

* cited by examiner

*Primary Examiner* — John Pak
(74) *Attorney, Agent, or Firm* — Michael Haynes PLC; Michael N. Haynes

(57) ABSTRACT

A method of making a composition having the property of being able to store chlorine dioxide includes mixing an aqueous chlorine dioxide solution with a superabsorbent, water-soluble polymer that is substantially unreactive with chlorine dioxide and permitting a mixture formed thereby to form one of a gel and a solid composition. A method of delivering chlorine dioxide includes providing a gel or solid composition as described and degelling the gel or dissolving the solid composition to dispense the chlorine dioxide therefrom. A method of disinfecting a target such as water, wastewater, or a surface comprises delivering chlorine dioxide as above and permitting the polymer to precipitate out of the mixture. Aqueous chlorine dioxide is then recovered and applied to the target.

41 Claims, 7 Drawing Sheets

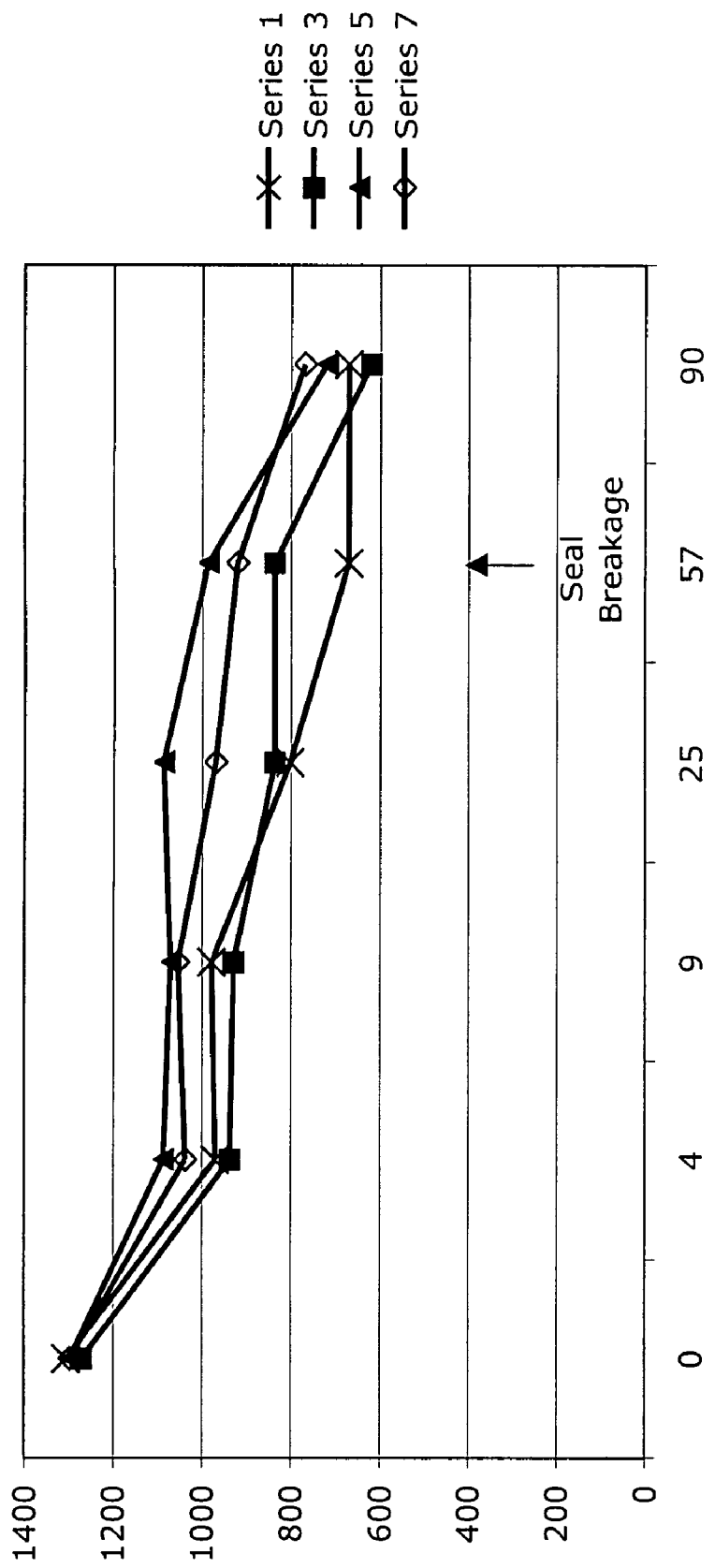
Figure 1a. Polymer Gels with High ClO2 Concentrations

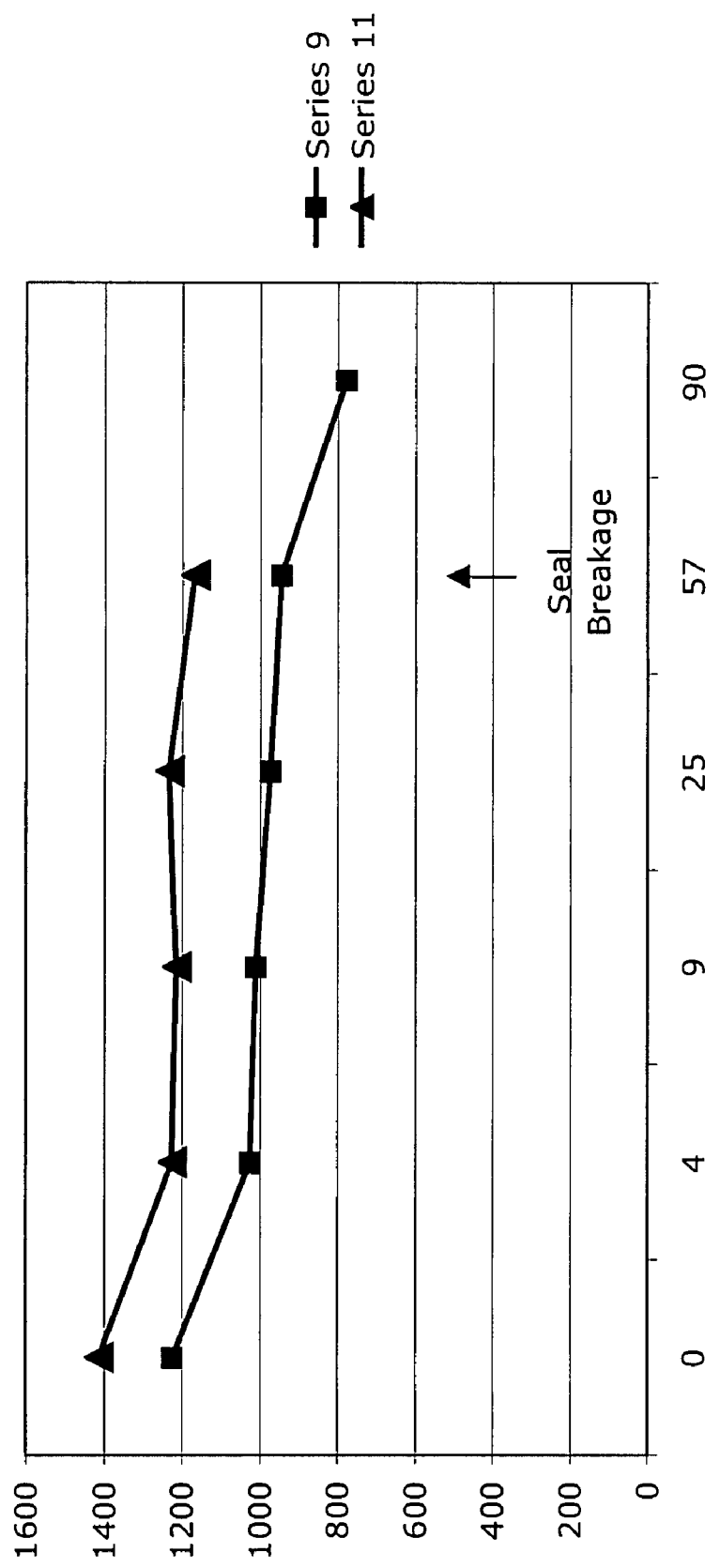
Figure 1b. Polymer Gels with High ClO2 Concentrations

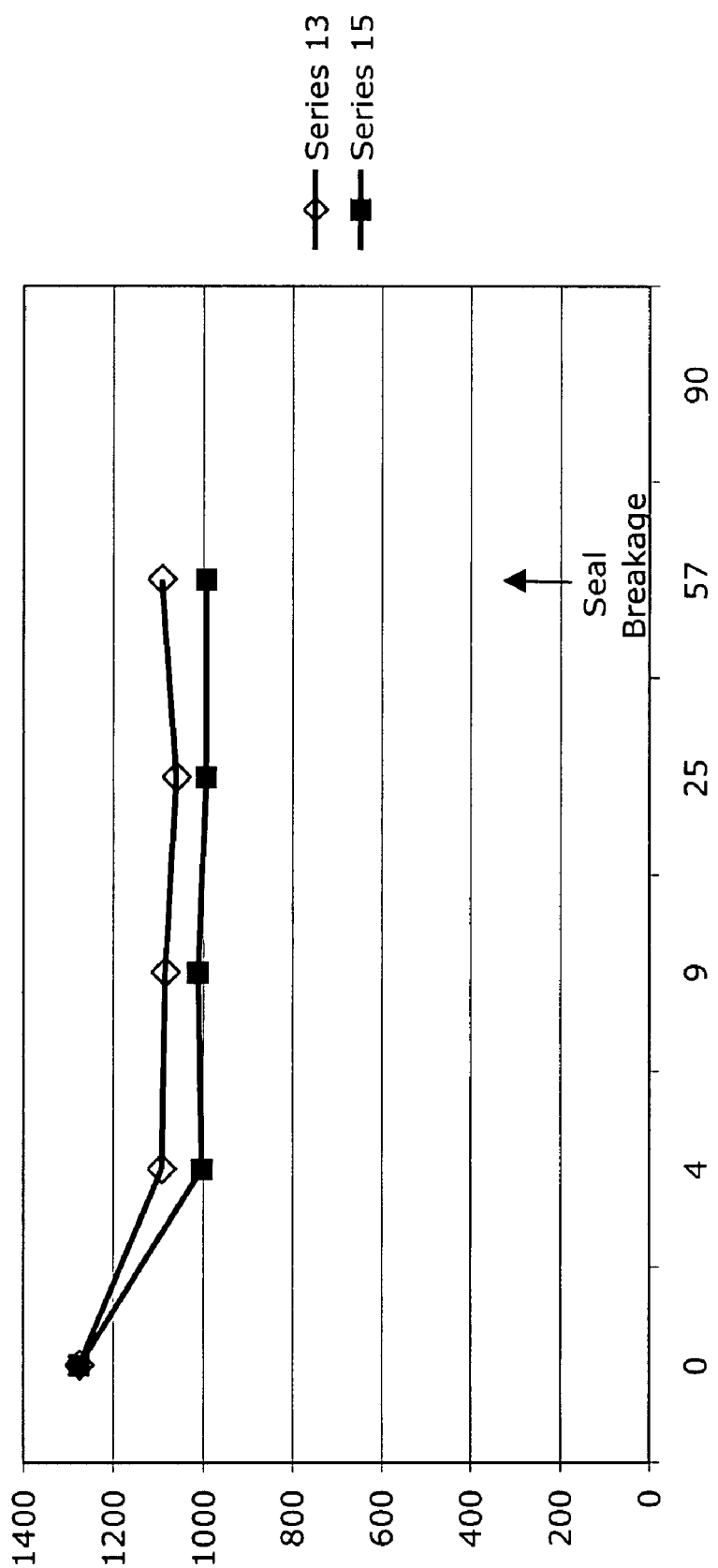

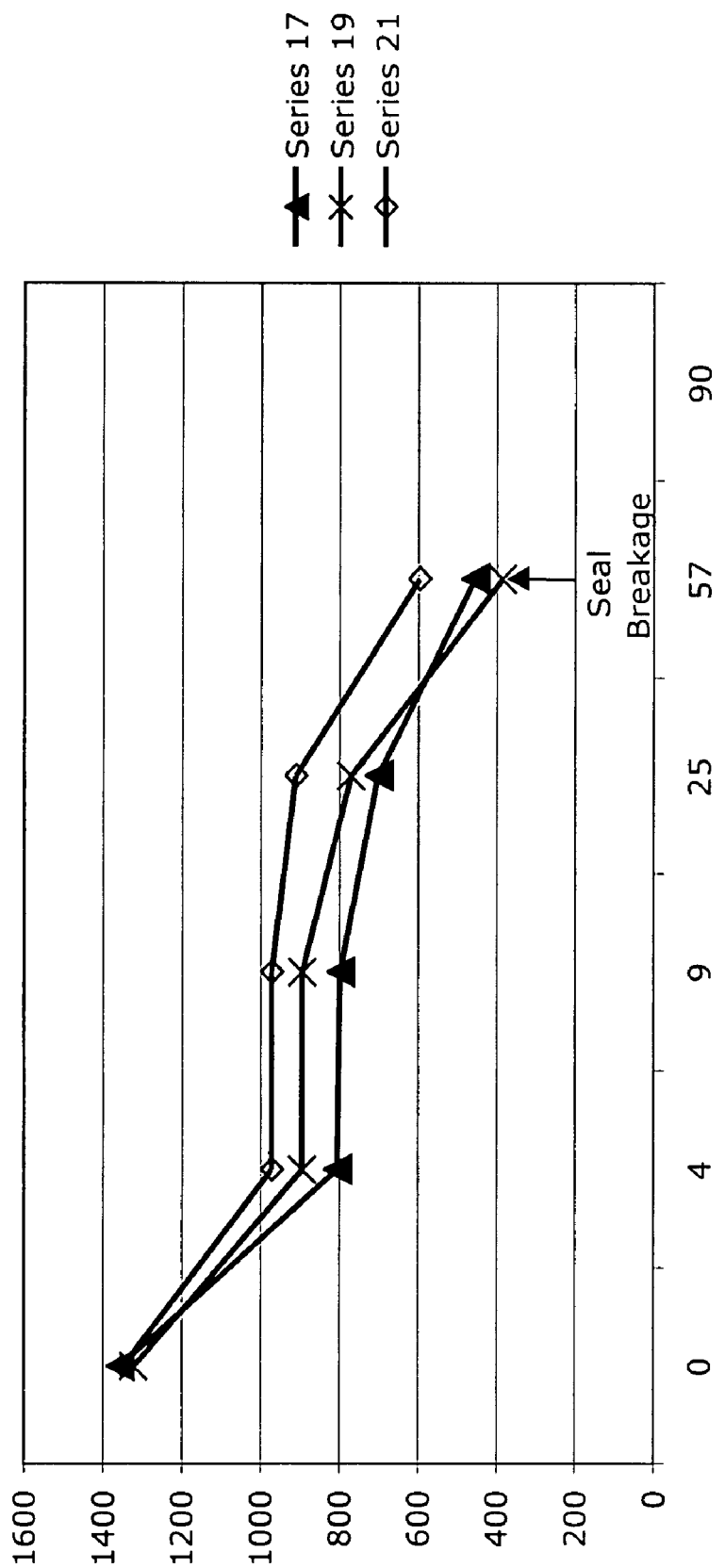
Figure 1d. Polymer Gels with High ClO2 Concentrations

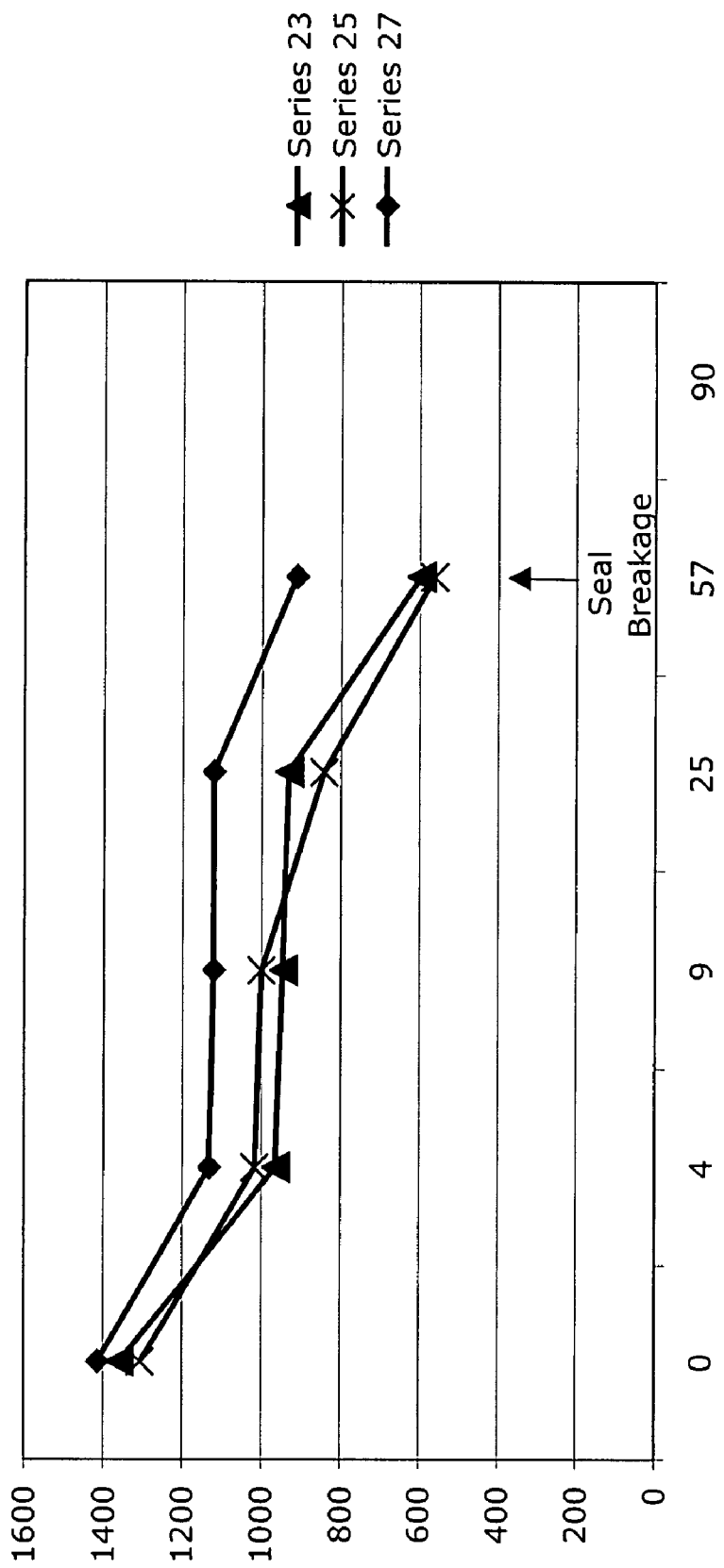
Figure 1e. Polymer Gels with High ClO2 Concentrations

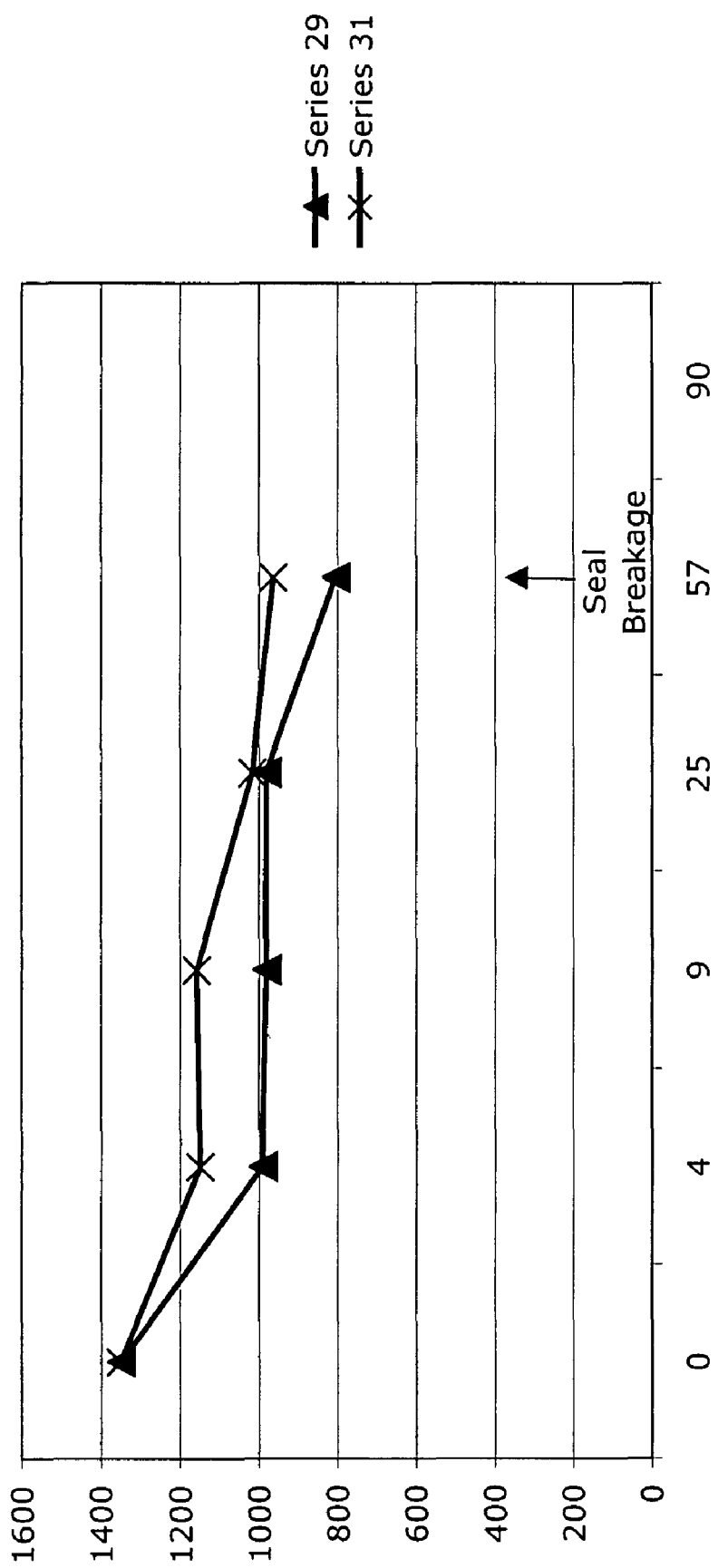

CHLORINE DIOXIDE GEL AND ASSOCIATED METHODS

CROSS-REFERENCE TO RELATED APPLICATIONS

This application is a continuation of, claims priority to, and incorporates herein by reference in its entirety, U.S. patent application Ser. No. 11/803,518 titled "Chlorine Dioxide Gel and Associated Methods", filed 15 May 2007 now U.S. Pat. No. 8,088,417, which is a Divisional of U.S. patent application Ser. No. 10/682,728, filed 9 Oct. 2003, now U.S. Pat. No. 7,229,647.

BACKGROUND OF THE INVENTION

1. Field of the Invention

The present invention relates to disinfectant compositions, and, more particularly, to a chlorine dioxide disinfectant composition, methods of use, and methods of making.

2. Description of Related Art

Many disinfectant compositions have been known in the art, most with some degree of undesirable side effects. For example, chlorine is an inexpensive and effective disinfectant; however, being highly reactive, chlorine generates precursors of carcinogens and disinfection byproducts. Chlorine is also a powerful bleach, is highly toxic, and is largely ineffective in disinfecting gram-positive bacteria. Chlorine's functions, in order of strength, include chlorination, oxidation, bleaching, and disinfection.

Ozone is primarily an oxidizer having limited disinfection capabilities in microbially contaminated water owing to its low solubility. Ultraviolet light (uv) is not effective in treating water that is microbially or biologically contaminated. Hydrogen peroxide, while being highly soluble in water, is not practical for use in water treatment. Bleach, although an effective bleaching and oxidizing agent, is highly reactive and is known to generate undesirable byproducts.

Chlorine dioxide does not possess any of the above-mentioned drawbacks, and is believed especially effective in water and wastewater treatment, and in aqueous solutions. Chlorine dioxide does not incur environmental problems or health concerns, and does not generate disinfection byproducts (DBPs), except for a small amount of chlorite ion ($ClO_2^-$) as an intermediate that spontaneously decomposes into harmless products, chloride ion ($Cl^-$) and oxygen. Further, chlorine dioxide does not create chlorinated organics, including precursor materials of trihalomethanes (THMs), unlike chlorine.

Chlorine dioxide is approximately five times more soluble than chlorine in water and direct exposure to the gas is much less harmful than to chlorine at similar concentrations. In addition, chlorine dioxide is very effective in disinfecting gram-positive bacteria, which cannot be treated effectively by other known disinfectants.

If used properly in its pure form, chlorine dioxide can produce residuals at an exit stream of a treatment system similar to those of chlorine, and is effective in reducing turbidity, discoloring, and deodorizing.

Chlorine dioxide made by prior art methods is known to be contaminated with free available chlorine (FAC), chlorite ion, chlorate ion, chloride ion, and hypochlorite ion, arising from process raw materials, process intermediates, and synthesis byproducts. Even if the contaminant concentrations are low, they may affect subsequent disinfection chemistry, as well as the stability of the chlorine dioxide product via a variety of chemical reactions, including oxidation-reduction reactions, as well as autocatalytic reactions. Some of these reactions include, but are not intended to be limited to:

$$Cl_2 + H_2O \rightleftharpoons HClO + HCl$$

$$HClO \rightleftharpoons H^+ + ClO^-$$

$$ClO_2 + ClO^- + e^- \rightleftharpoons 2Cl^- + 3/2 O_2$$

$$ClO_2 + ClO_2^- + e^- \rightleftharpoons 2Cl^- + 2O_2$$

$$ClO_2 + e^- \rightleftharpoons Cl^- + O_2$$

$$ClO_3^- \rightleftharpoons ClO_2^- + (O)$$

$$ClO_2 + (O) \rightleftharpoons Cl^- + 3/2 O_2$$

The presence of other oxychloro compounds in the chlorine dioxide aqueous solution can lead to many other chemical reactions that are undesirable for the intended objects of the product. Such reactions not only create harmful byproducts, but also can cause the premature decomposition of the product chlorine dioxide.

Chlorine dioxide is not stable as a product gas, being susceptible to uv and to self-decomposition into chlorine and oxygen. Therefore, chlorine dioxide has typically been in aqueous solution, limiting its applications.

Even in aqueous solution chlorine dioxide is unstable, further limiting its use as a liquid product. Owing to its instability, chlorine dioxide has never been approved as a transportation chemical by the U.S. Department of Transportation or the United Nations. Thus on-site generation has been the only means for utilizing chlorine dioxide, which must be used within a day or two at most, 80-90% of its strength typically lost within 24 hours. The decomposition mechanisms have not until now been understood.

Decomposition of chlorine dioxide may be attributed to six possible causes:

1. Chlorine dioxide exhibits vapor-phase (or dry-phase) decomposition.
2. Gas-phase decomposition of chlorine dioxide is promoted in the presence of air, specifically, oxygen. In aqueous solution, the dissolved oxygen concentration being only ~9.2 mg/L, decomposition is less.
3. Decomposition in both the dry and wet phases is also promoted in the presence of other strong oxidants and reducing agents. Although chlorine dioxide is generally an oxidant, it can function as a reducing agent when in contact with a stronger oxidizer. Therefore, any impurities in the product stream or solution would participate in a chemical reaction, including decomposition of chlorine dioxide. Once decomposition begins, the decomposition products, including oxygen, act to promote further decomposition reactions. Such an accelerated reaction is termed "autocatalytic," meaning that the undesirable reactions are self-sustaining, eventually leading to substantially complete decomposition of the chlorine dioxide in the system.
4. Chlorine dioxide decomposition is promoted by uv irradiation, since the molecules readily absorb radiation.
5. Chlorine dioxide decomposition is very strongly promoted by mechanical agitation or shock, which can be compounded by oxygen-triggered decomposition as described in (2) above, since mechanical agitation can create air pockets and increase the concentration of dissolved oxygen in the water.
6. Chlorine dioxide decomposition is greater in a container having a large headspace, driven by the vapor pressure of chlorine dioxide, promoting movement from the aqueous phase to the vapor phase.

Pure chlorine dioxide is known to be produced by the system and method of commonly owned U.S. Pat. Nos. 5,855,861 and 6,051,135, the contents of which are incorporated herein by reference. There are, however, no known systems, compositions, or methods for achieving long-term storage and preservation of pure chlorine dioxide, which would be desirable.

SUMMARY OF THE INVENTION

The present invention is directed to a stable chlorine dioxide composition, its method of making, and method of use, for achieving long-term storage and subsequent release when desired.

The invention includes a method of making a composition having the property of being able to store chlorine dioxide, preferably for long periods. The method comprises the steps of mixing an aqueous chlorine dioxide solution with a superabsorbent, water-soluble polymer that is substantially unreactive with chlorine dioxide and permitting a mixture formed thereby to form one of a gel and a solid composition. The composition comprises the gel or solid composition formed thereby. The solid composition may be made into pellets or tablets, for example.

A method of delivering chlorine dioxide comprises the steps of providing a gel or solid composition as described above and degelling the gel or dissolving the solid composition to dispense the chlorine dioxide therefrom.

A method of disinfecting a target such as water, wastewater, or a surface comprises the steps of delivering chlorine dioxide by providing and degelling the gel or dissolving the solid composition as above, and permitting the polymer to precipitate out. Aqueous chlorine dioxide is then recovered from a supernatant above the precipitate, and the recovered aqueous chlorine dioxide is applied to the target.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

FIG. 1 graphs chlorine dioxide concentration versus time for series of polymer gels for Example 3.

DETAILED DESCRIPTION OF THE PREFERRED EMBODIMENTS

Figure 2:
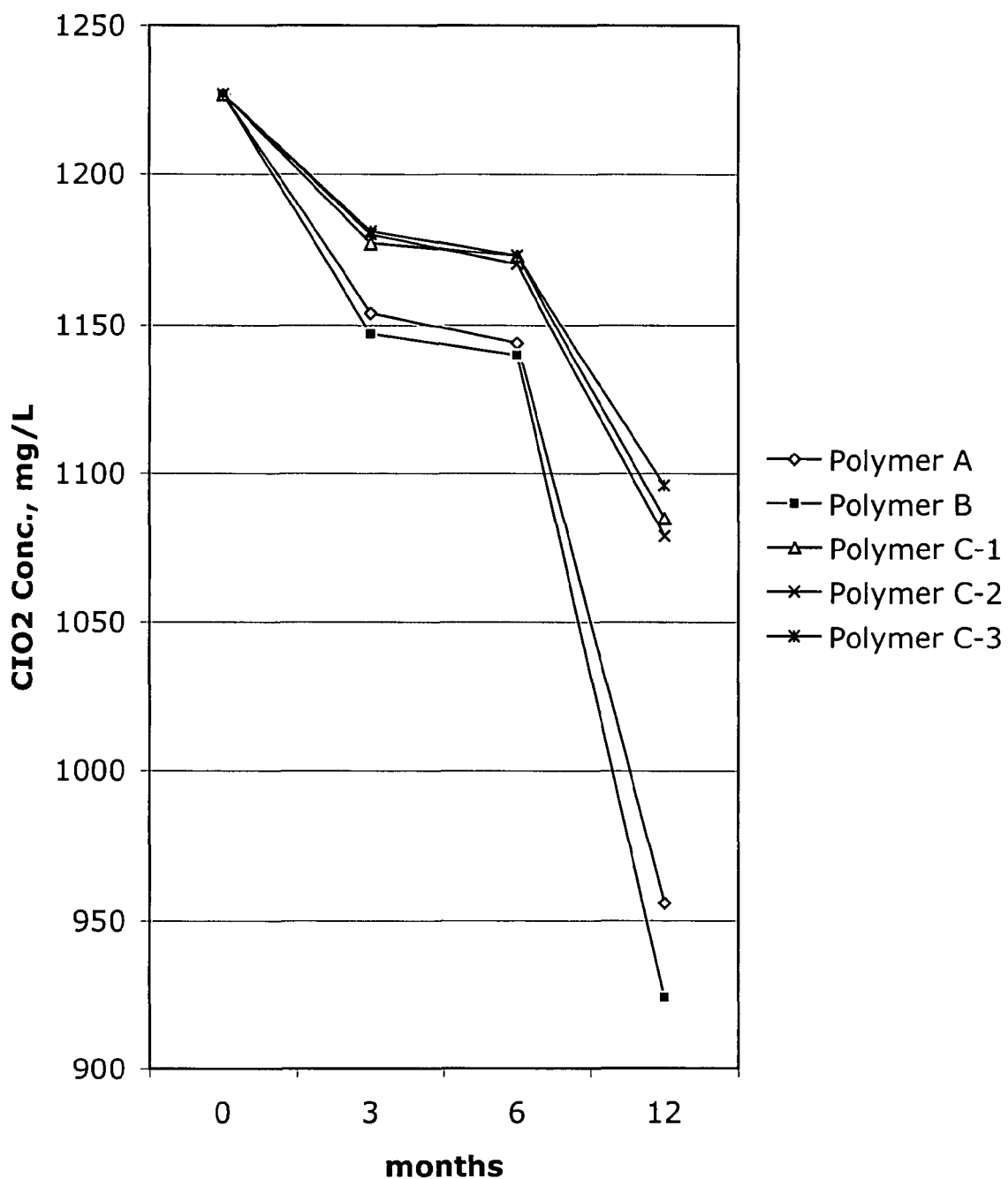
FIG. 2 graphs chlorine dioxide concentration versus time for series of polymer gels for Example 4.

A description of the preferred embodiments of the present invention will now be presented with reference to FIGS. 1 and 2.

The present invention is directed to a stable chlorine dioxide gel or solid composition, its method of making, and method of use, for achieving long-term storage and subsequent release when desired. The invention is also directed to a method of disinfecting a target, such as, but not intended to be limited to, water, wastewater, or a surface.

Broadly, the gel and solid composition of the present invention are made by absorbing substantially byproduct-free and FAC-free, pure aqueous chlorine dioxide solution in a superabsorbent or water-soluble polymer that is nonreactive with chlorine dioxide in a substantially oxygen-free environment. If the product is a gel, the gel retains a color substantially identical with that of the original chlorine dioxide solution, that is, yellowish-green for 200-600 mg/L, bright green for 1000-2500 mg/L, and dark green to greenish brown for >5000 mg/L. As tested thus far, product gel retains its consistency for more than a year, essentially permanently under a controlled environment, retaining the chlorine dioxide concentration at 80% or higher for at least 6 months at room temperature.

The gel and solid compositions of the present invention are believed to retain chlorine dioxide by "locking" the chlorine dioxide molecules in an inert and innocuous solid matrix such as a gel or tablet. Such a matrix limits the mobility of the thus-entrapped molecules, making them less susceptible to mechanical shock, protects against uv or ir radiation, and limits air/oxygen penetration. The gel should not have microbubbles or air globules present, and preferably the amount of polymer material required should be sufficiently small so as to make the resulting product cost-effective. Any decomposition that does occur should preferably yield only harmless chloride ion and oxygen. For example,

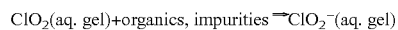

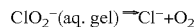

Although the gel form of the product is believed to represent the preferred embodiment, the composition may also comprise a tablet in an alternate embodiment of a solid composition. Such a tablet is created by substantially the same method as for the gel; however, a greater proportion of the superabsorbent polymer is used, e.g., $\geq 50$ wt. %, with $\leq 50$ wt. % $ClO_2$ added.

The superabsorbent polymer of the present invention should not be able to undergo an oxidation reaction with chlorine dioxide, and should be able to liberate chlorine dioxide into water without any mass transfer resistance. Nor should byproduct be releasable from the gel in contact with fresh water. Exemplary polymers may comprise at least one of a sodium salt of poly(acrylic acid), a potassium salt of poly(acrylic acid), straight poly(acrylic acid), poly(vinyl alcohol), and other types of cross-linked polyacrylates, such as polyacrylimide and poly(chloro-trimethylaminoethyl acrylate), each being preferably of pharmaceutical grade. A molecular weight range is preferably 5,000-150,000, and more preferably 15,000-40,000 for forming a gel, and $\geq 50,000$ for forming a solid composition. It is believed that sodium salts are preferable to potassium salts for any potential byproduct release, although such a release has not been observed. The amount of polymer required to form a stable gel is in the order of sodium and potassium salts of poly (acrylic acid)<straight poly(acrylic acid)<poly(vinyl alcohol). The order of stability is in reverse order, however, with very little difference among these polymer types.

The gel of the present invention is formed by mixing a mass of the polymer into the aqueous chlorine dioxide solution in an amount preferably less than 5-10%, most preferably in range of approximately 0.5-5%, and stirring sufficiently to mix the components but sufficiently mildly so as to minimize the creation of agitation-produced bubbles. Gelling efficiency varies among the polymers, with the poly(acrylic acid) salts (Aridall and ASAP) forming gels more quickly with less polymer, a ratio of 100:1 solution:resin sufficient for making a stable gel; straight poly(acrylic acid) requires a ratio of 50:1 to make a similarly stable gel. The stabilities here refer to mechanical and structural, not chemical, stability.

The gelling process typically takes about 0.5-4 min, preferably 2 min, with a minimum time of mixing preferable. Gels can be produced without mixing; however, mild agitation assists the gelling process and minimizes gelling time. It has been found that 1 g of polymer can be used with as much as 120 g of 2000-ppm pure chlorine dioxide solution. Concentrations of at least 5000 ppm are achievable.

Any bubbles that are produced are found to be very stable, taking 2-3 weeks to migrate to the top of a container, which is 6-7 orders of magnitude slower than bubbles in an aqueous chlorine dioxide solution.

Preferably the mixing is carried out in a substantially air/oxygen-free environment in a closed container, possibly nitrogen-purged. Storage of the formed gel should be in sealed containers having uv-blocking properties is preferred, such containers comprising, for example, uv-blocking amber glass, opaque high-density polyethylene, chlorinated poly(vinyl chloride) (CPVC), polytetrafluoroethylene-lined poly-ethylene-(PTFE) lined polyethylene, cross-linked polyethylene, polyvinyl chloride, and polyvinylidenefluoride (PVDF), although these are not intended to be limiting.

The gel of the present invention was found to be very effective in preserving chlorine dioxide concentration for long periods of time, in sharp contrast to the 1-2 days of the aqueous solution. The clean, bright green color of the gel is retained throughout storage, and did not substantially degas as found with aqueous solutions of similar concentration. For example, a 400-ppm aqueous solution produces a pungent odor that is not detectable in a gel of similar concentration. The straight PAA gels made from Carbopol (Polymer C; Noveon, Inc., Cleveland, Ohio) were found to achieve better preservation than the PAA salt types. Additional resins that may be used include, but are not intended to be limited to, Aridall and ASAP (BASF Corp., Charlotte, N.C.), and poly(vinyl alcohol) (A. Schulman, Inc., Akron, Ohio).

The liberating of aqueous chlorine dioxide from the gel material is performed by stirring the gel material into deionized water, and sealing and agitating the mixing vessel, for example, for 15 min on a low setting. Polymer settles out in approximately 15 min, the resulting supernatant comprising substantially pure aqueous chlorine dioxide. The gellant is recoverable for reuse.

Aqueous chlorine dioxide is liberated from a tablet by dissolving the tablet into deionized water and permitting the polymer to settle out as a precipitate.

The resulting aqueous chlorine dioxide may then be applied to a target, such as, but not limited to, water, wastewater, or a surface.

In order to minimize decomposition, both spontaneous and induced, the components of the gel and solid composition should be substantially impurity-free. As an example, the chlorine dioxide solution may be provided by use of the method of the '861 and '135 patents referred to above. Exposure to air/oxygen and uv and ir radiation should be minimized, as should mechanical shock and agitation.

Laboratory data are discussed in the following four examples.

Example 1

Two types of polymer, the sodium and potassium salts of poly(acrylic acid), were used to form gels. The aqueous chlorine dioxide was prepared according to the method of the '861 and '135 patents, producing a chlorine dioxide concentration of 4522 mg/L, this being diluted as indicated.

The gels were formed by mild shaking for 2 min in an open clock dish, the gels then transferred to amber glass bottles, leaving minimum headspace, sealed, and stored in the dark. The aqueous controls were stored in both clear and amber bottles. After 3 days it was determined that the gels retained the original color and consistency, and were easily degelled. Table 1 provides data for 3 and 90 days, illustrating that little concentration loss occurred. The samples after 3 days were stored under fluorescent lighting at approximately 22° C.

TABLE 1

Chlorine Dioxide Gels in 3- and 90-Day Storage, Concentrations in ppm

|  | Container | $ClO_2$ Amt. (ml) | Polymer Amt. (g) | Initial $ClO_2$ Conc. | $ClO_2$ Conc. After 3 Days | $ClO_2$ Conc. After 90 Days | Prod. Form |
| --- | --- | --- | --- | --- | --- | --- | --- |
| Aqueous Soln. | Clear Bottle | 35 | — | ~420 | ~60 | ~0 | Soln. |
| Aqueous Soln. | Amber Bottle | 35 | — | ~420 | ~370 | ~70 | Soln. |
| Polymer BA1-1 | Amber Bottle | 35 | 0.25 | ~400 | ~390 | ~380 | Gel |
| Polymer BA1-2 | Amber Bottle | 35 | 0.30 | ~380 | ~350 | ~350 | Gel |
| Polymer BA2-1 | Amber Bottle | 35 | 0.25 | ~380 | ~350 | ~330 | Gel |
| Polymer BA2-2 | Amber Bottle | 35 | 0.30 | ~380 | ~360 | ~355 | Gel |

BA1: Sodium polyacrylate, ASAP ™ (BASF)
BA2: Potassium polyacrylate, Aridall ™ (BASF)

From these data it may be seen that, even when stored in a tightly sealed, amber bottle, the aqueous solution loses strength rapidly, although the amber bottle clearly provides some short-term alleviation of decomposition.

Also, even with a 0.71% proportion of gelling material, a stable gel was formed. The gels, in the order presented in Table 1, retained 97.4, 100, 94.3, and 98.6% of their strength at 3 days after 90 days. The two polymers provided essentially equal effectiveness. The gels apparently protected against uv-mediated decomposition. The gels are also far more effective in preserving chlorine dioxide concentration.

The gels were shown to preserve their original color during the storage period. Analysis after 90 days proved that the degelled solution contained only chlorine dioxide and a very small amount of chloride ion.

Example 2

Gels formed by five different polymers, each having their formed gels stored in clear and amber containers, were compared when stored under different conditions. Table 2 provides the results of these experiments.

TABLE 2

Results of Experiments of Example 2

| # of Days | 10 | 14 | 21 | 28 | 32 | 39 | 51 | 102 |
|---|---|---|---|---|---|---|---|---|
| CONTROL 1 | 407 | 414 | 380 | 332 | 312 | 282 | 288 | 277 |
| STDEV | 0.0 | 11.7 | 12 | 5.9 | 11.7 | 5.9 | 5.9 | 6.6 |
| CONTROL 2 | 332 | 271 | 278 | 261 | 265 | 292 | 282 | 280 |
| STDEV | 11.7 | 23.5 | 12 | 5.9 | 10.2 | 11.7 | 15.5 | 10.0 |
| CONTROL 3 | 286 | 241 | 229 | 225 | 221 | 233 | 225 | 219 |
| STDEV | 0.0 | 0.0 | 0.0 | 6.6 | 6.6 | 6.6 | 6.6 | 5.9 |
| HALF BOTTLE | 331 | 292 | 280 | 235 | 254 | 263 | 205 | 144 |
| STDEV | 25.7 | 11.6 | 9 | 10.4 | 10.2 | 12.6 | 7.8 | 7.1 |
| Polymer A | 257 | 248 | 236 | 214 | 208 | 208 | 201 | 197 |
| STDEV | 12.8 | 7.4 | 7 | 14.8 | 6.4 | 9.8 | 7.4 | 8.8 |
| Polymer B | 228 | 216 | 208 | 196 | 198 | 194 | 192 | 184 |
| STDEV | 0.0 | 0.0 | 7 | 6.9 | 12.0 | 6.9 | 12.0 | 6.5 |
| Polymer C-1 | 317 | 283 | 278 | 266 | 270 | 278 | 270 | 271 |
| STDEV | 7.4 | 12.8 | 7 | 7.4 | 11.1 | 7.4 | 12.9 | 10.2 |
| Polymer C-2 | 287 | 291 | 287 | 261 | 257 | 259 | 257 | 254 |
| STDEV | 7.4 | 7.4 | 7 | 7.4 | 0.0 | 3.7 | 0.0 | 4.9 |
| PPM lost due to separation of polymer (CONTROL 2-CONTROL 3) Average = 48 | 46 | 31 | 49 | 36 | 43 | 59 | 56 | 61 |

CONTROL 1: Full amber bottle with polymer (no agitation)
CONTROL 2: Full amber bottle prepared with polymer samples (agitated for 15 min)
CONTROL 3: Full amber bottle prepared with polymer samples (agitated for 15 min) and analyzed with polymer samples (diluted and agitated 15 min)
HALF: Half-filled amber bottle
POLYMER A: Sodium polyacrylate, ASAP (BASF); full amber bottle with 0.25 g ASAP (agitated 15 min for preparation and diluted and agitated 15 min for analysis)
POLYMER B: Potassium polyacrylate; full amber bottle with 0.30 g Aridall (BASF) (agitated 15 min for preparation and diluted and agitated 15 min for analysis)
CARBOPOL C-1: Poly(acrylic acid); full amber bottle with 0.50 g Carbopol ® 974 (Noveon) (agitated 15 min for preparation and diluted and agitated 15 min for analysis)
CARBOPOL C-2: Poly(acrylic acid); Full amber bottle with 0.75 g Carbopol ® 971 (Noveon) (agitated 15 min for preparation and diluted and agitated 15 min for analysis)

The half-bottle results indicate that stability was significantly lower than in full-bottle samples under substantially identical preparation and storage conditions, the difference being even more pronounced with longer storage times, illustrating the decomposition effect triggered by gas-phase air. Even in the half-bottle gels, however, storage effectiveness is still 100-200 times that of conventional solution storage.

Example 3

High-concentration (1425 ppm) aqueous chlorine dioxide was used to form polymer gels as listed in Table 3 in this set of experiments, the results of which are given in Table 4 and FIG. 1. The initial loss of concentration strength is due to dilution and procedural exposure, during preparation and analysis, to ambient air, not to decomposition based upon interaction between the polymer and the chlorine dioxide.

TABLE 3

Sample Preparation Information for Gel Technology (High Concentration)

| Samples | Bottle | Gellant |
|---|---|---|
| HDA | Amber | Polymer A |
| HDB | Amber | Polymer B |
| HDC | Amber | Polymer C-1 |
| HDD | Amber | Polymer C-2 |
| HDE | Amber | Polymer C-3 |
| HDF | Amber | Control 1 |
| HDG | Amber | Control 2 |
| HDH | Amber | Control 3 |
| HDI | Clear | Polymer A |
| HDJ | Clear | Polymer B |
| HDK | Clear | Polymer C-1 |
| HDL | Clear | Polymer C-2 |
| HDM | Clear | Polymer C-3 |
| HDN | Clear | Control 1 |
| HDO | Clear | Control 2 |
| HDP | Clear | Control 3 |

Note:
All sample bottles are full, and stored at room temperature under fluorescent light.

TABLE 4

$ClO_2$ Analysis Data of $ClO_2$ Gels

| | TRT | Initial | 4 d | 9 d | 25 d | 57 d | 90 d | Series |
|---|---|---|---|---|---|---|---|---|
| HDA | 1425 | 1306 | 971 | 979 | 803 | 670 | 670 | 1 |
| | | 0 | 24 | 12 | 0 | 0 | 0 | |
| HDB | 1425 | 1272 | 937 | 929 | 837 | 837 | 619 | 3 |
| | | 0 | 0 | 12 | 0 | 0 | 24 | |
| HDC | 1425 | 1297 | 1088 | 1071 | 1088 | 988 | 720 | 5 |
| | | 12 | 24 | 0 | 24 | 24 | 24 | |
| HDD | 1425 | 1297 | 1038 | 1055 | 971 | 921 | 770 | 7 |
| | | 12 | 47 | 0 | 0 | 24 | 47 | |
| HDE | 1425 | 1225 | 1026 | 1010 | 973 | 944 | 778 | 9 |
| | | 0 | 0 | 23 | 0 | 23 | 23 | |
| HDF | 1425 | 1414 | 1227 | 1215 | 1234 | 1169 | | 11 |
| | | 17 | 17 | 0 | 0 | 0 | | |
| HDG | 1425 | 1275 | 1093 | 1084 | 1059 | 1093 | | 13 |
| | | 23 | 0 | 12 | 0 | 0 | | |
| HDH | 1425 | 1275 | 1002 | 1010 | 993 | 993 | | 15 |
| | | 23 | 12 | 23 | 0 | 0 | | |
| HDI | 1425 | 1358 | 806 | 798 | 701 | 456 | | 17 |
| | | 12 | 0 | 12 | 0 | 0 | | |
| HDJ | 1425 | 1323 | 894 | 894 | 771 | 386 | | 19 |
| | | 12 | 25 | 25 | 0 | 50 | | |
| HDK | 1425 | 1350 | 973 | 973 | 911 | 596 | | 21 |
| | | 0 | 12 | 12 | 0 | 0 | | |
| HDL | 1425 | 1358 | 964 | 946 | 932 | 596 | | 23 |
| | | 12 | 25 | 0 | 0 | 0 | | |
| HDM | 1425 | 1306 | 1017 | 999 | 841 | 561 | | 25 |
| | | 12 | 0 | 25 | 0 | 0 | | |
| HDN | 1425 | 1414 | 1133 | 1122 | 1122 | 911 | | 27 |
| | | 17 | 17 | 0 | 0 | 33 | | |
| HDO | 1425 | 1350 | 990 | 982 | 982 | 806 | | 29 |
| | | 25 | 12 | 0 | 0 | 0 | | |
| HDP | 1425 | 1350 | 1148 | 1157 | 1017 | 964 | | 31 |
| | | 25 | 12 | 0 | 0 | 25 | | |

Note:
Data in the first row for each sample are averages, while those on the second row are standard deviations. Sample designations as in Table 3.

The data indicate that the gels are quite stable for a long period of time. In most cases the gels retained their strength at 50% or higher even after 90 days, which is believed to represent a technological breakthrough.

Amber bottles are clearly more effective in preserving chlorine dioxide concentration, especially until the 60-day mark. Some late-stage decline may be attributable to seal failure, the seals used in these experiments comprising paraffin, which is known to be unreliable with regard to drying, fracture, pyrolytic evaporation, and puncture, and some of this failure was observable to the naked eye.

The high-molecular-weight polymer, poly(acrylic acid) (polymer C) was more effective than its lower-molecular-weight counterparts, the PAA salts (polymers A and B), indicating that higher-molecular-weight polymers provide better structural protection and "caging" for chlorine dioxide molecules against uv and air.

Example 4

The long-term stability of the gels of the present invention was tested using a set of gels prepared from three different types of water-soluble polymers. The prepared samples were kept in a ventilated cage with fluorescent light on full-time at room temperature. The gel samples were sealed tightly in amber bottles with paraffinic wax and wrapped with Teflon tapes for additional protection. Five identical samples using each polymer type were prepared, and one each was used for analysis at the time intervals shown in Table 5 and FIG. 2.

TABLE 5

Long-term Stability of Chlorine Dioxide Gels

| | 0 mo. | 3 mo. | 6 mo. | 12 mo. |
|---|---|---|---|---|
| Polymer A | 1227 | 1154 | 1144 | 956 |
| Polymer B | 1227 | 1147 | 1140 | 924 |
| Polymer C-1 | 1227 | 1177 | 1173 | 1085 |
| Polymer C-2 | 1227 | 1180 | 1170 | 1079 |
| Polymer C-3 | 1227 | 1181 | 1173 | 1096 |

Polymers A and B were added at 0.8% of the solution mass, with Polymer C added at 2%, to achieve optimal gelling concentration for each individual polymer.

All the samples indicate long-term chlorine dioxide product stability previously unachievable in the art. The gels made from polymer C were better in long-term preservation of chlorine dioxide than those made using polymers A and B, which may be attributable to its higher average molecular weight, as well as to the greater amount of polymer used per unit volume.

Therefore, it will be appreciated by one of skill in the art that there are many advantages conferred by the present invention. Chlorine dioxide is preserved at least 200, and up to 10,000, times longer than previously possible in aqueous solution. Off-site manufacturing and transport now becomes possible, since the composition is unaffected by vibration and movement, is resistant to uv and ir radiation, to bubble formation, and to oxygen penetration, and reduces vapor pressure. The composition has substantially reduced risks from inhalation and skin contact.

The applications of the present invention are numerous in type and scale, and may include, but are not intended to be limited to, industrial and household applications, and medical, military, and agricultural applications. Specifically, uses may be envisioned for air filter cartridges, drinking water, enclosed bodies of water, both natural and manmade, cleansing applications in, for example, spas, hospitals, bathrooms, floors and appliances, tools, personal hygiene (e.g., for hand cleansing, foot fungus, gingivitis, soaps, and mouthwash), and food products. Surfaces and enclosed spaces may be cleansed, for example, against gram-positive bacteria, spores, and anthrax.

It may be appreciated by one skilled in the art that additional embodiments may be contemplated without departing from the spirit of the invention.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the composition and associated methods described herein are by way of example, and the scope of the invention is not limited to the exact details disclosed.

The invention claimed is:

1. A method comprising:
   in a substantially oxygen-free environment, substantially entrapping a substantially impurity-free aqueous chlorine dioxide solution in a superabsorbent polymer that is substantially unreactive with chlorine dioxide; and
   storing a mixture formed by said entrapping in a storage container having ultraviolet radiation blocking properties, said mixture, while stored in said storage container, adapted to retain a chlorine dioxide concentration value, relative to an initial chlorine dioxide concentration value of said mixture when initially mixed, of 50% or higher for at least 90 days.

2. The method recited in claim 1, further comprising, mixing said aqueous chlorine dioxide solution and said superabsorbent polymer.

3. The method recited in claim 1, further comprising, mixing said aqueous chlorine dioxide solution and said superabsorbent polymer in a nitrogen-purged container.

4. The method recited in claim 1, further comprising, absorbing said aqueous chlorine dioxide solution into said superabsorbent polymer.

5. The method recited in claim 1, further comprising, pouring said aqueous chlorine dioxide solution into a mixing container, and degassing said mixing container during said pouring.

6. The method recited in claim 1, wherein said superabsorbent polymer comprises at least one member of a group consisting of: a sodium salt of poly(acrylic acid), a potassium salt of poly(acrylic acid), straight poly(acrylic acid), poly(vinyl alcohol), polyacrylamide, and poly(chloro-trimethylaminoethyl acrylate).

7. The method recited in claim 1, wherein said superabsorbent polymer is of pharmaceutical grade.

8. The method recited in claim 1, wherein said superabsorbent polymer has a powder form or a pellet form.

9. The method recited in claim 1, wherein said aqueous chlorine dioxide solution is substantially entrapped in a solid matrix formed from said superabsorbent polymer.

10. The method recited in claim 1, wherein said mixture is formed in an environment substantially free from ultraviolet radiation.

11. The method recited in claim 1, wherein said mixture is formed so as to minimize agitation and consequent formation of bubbles.

12. The method recited in claim 1, wherein said mixture is formed at approximately room temperature.

13. The method recited in claim 1, wherein said mixture is formed at a temperature less than 20° C.

14. The method recited in claim 1, wherein said mixture has a chlorine dioxide concentration of up to 5000 mg/L.

15. The method recited in claim 1, wherein said storage container comprises at least one member of a group consisting of: uv-blocking amber glass, opaque high-density polyethylene, chlorinated poly(vinyl chloride), polytetrafluoroethylene-lined polyethylene, cross-linked polyethylene, polyvinyl chloride, and polyvinylidenefluoride.

16. The method recited in claim 1, wherein said storing comprises providing a substantially oxygen-free environment in said storage container.

17. The method recited in claim 1, wherein said storing comprises filling said storage container to achieve minimum headspace therein.

18. The method recited in claim 1, further comprising retaining said storage container containing said mixture in a condition to minimize agitation.

19. A stored chlorine dioxide-containing mixture formed by the method of claim 1.

20. A stored chlorine dioxide-containing solid formed by the method of claim 1.

21. A method comprising storing a mixture in a storage container having ultraviolet radiation blocking properties, said mixture formed from mixing, in a substantially oxygen-free environment, a substantially impurity free aqueous chlorine dioxide solution with a superabsorbent polymer that is substantially unreactive with chlorine dioxide, said mixture comprising a solid matrix formed from said superabsorbent polymer, said solid matrix substantially entrapping said aqueous chlorine dioxide solution, said mixture, while stored in said storage container, adapted to retain a chlorine dioxide concentration value, relative to an initial chlorine dioxide concentration value of said mixture when initially mixed, of 50% or higher for at least 90 days.

22. A method comprising:
   in a substantially oxygen-free environment, in a mixture comprising a substantially impurity free aqueous chlorine dioxide solution and a superabsorbent polymer that is substantially unreactive with chlorine dioxide, substantially entrapping said aqueous chlorine dioxide solution in a solid matrix formed from said superabsorbent polymer; and
   storing said mixture in a storage container having ultraviolet radiation blocking properties, said mixture, while stored in said storage container, adapted to retain a chlorine dioxide concentration value, relative to an initial chlorine dioxide concentration value of said mixture when initially mixed, of 50% or higher for at least 90 days.

23. A system comprising a storage container having ultraviolet radiation blocking properties and containing a mixture formed from a superabsorbent polymer and a substantially impurity free aqueous chlorine dioxide solution, said superabsorbent polymer substantially entrapping said aqueous chlorine dioxide solution, said superabsorbent polymer substantially unreactive with chlorine dioxide, said chlorine dioxide and said superabsorbent polymer mixed in a substantially oxygen-free environment, said mixture, while stored in said storage container, adapted to retain a chlorine dioxide concentration value, relative to an initial chlorine dioxide concentration value of said mixture when initially mixed, of 50% or higher for at least 90 days.

24. The system recited in claim 23, wherein said superabsorbent polymer is selected from a group consisting of: a sodium salt of poly(acrylic acid), a potassium salt of poly(acrylic acid), straight poly(acrylic acid), poly(vinyl alcohol), polyacrylamide, and poly(chloro-trimethylaminoethyl acrylate).

25. The system recited in claim 23, wherein said superabsorbent polymer is of pharmaceutical grade.

26. The system recited in claim 23, wherein, in said mixture, a concentration of said superabsorbent polymer is $\geq 50$ wt. % of said aqueous chlorine dioxide solution.

27. The system recited in claim 23, wherein said mixture has said chlorine dioxide concentration of up to 5000 mg/L.

28. The method recited in claim 23, wherein said aqueous chlorine dioxide solution is substantially entrapped in a solid matrix formed from said superabsorbent polymer.

29. The system recited in claim 23, wherein said storage container comprises at least one member of a group consisting of: uv-blocking amber glass, opaque high-density polyethylene, chlorinated poly(vinyl chloride), polytetrafluoroethylene-lined polyethylene, cross-linked polyethylene, polyvinyl chloride, and polyvinylidenefluoride.

30. The system recited in claim 23, wherein said storage container is sealed to achieve a substantially oxygen-free environment therein.

31. The system recited in claim 23, wherein said storage container is adapted to maintain a substantially oxygen-free environment when said mixture is stored therein.

32. A method comprising liberating aqueous chlorine dioxide from a mixture comprising a superabsorbent polymer substantially entrapping a substantially impurity-free aqueous chlorine dioxide solution, said superabsorbent polymer substantially unreactive with chlorine dioxide, said chlorine dioxide and said superabsorbent polymer mixed in a substantially oxygen-free environment to form said mixture, when stored in a storage container having ultraviolet radiation blocking properties, said mixture adapted to retain a chlorine dioxide concentration value, relative to an initial chlorine dioxide concentration value of said mixture when initially mixed, of 50% or higher for at least 90 days.

33. The method recited in claim 32, further comprising dissolving said mixture in water.

34. The method recited in claim 32, further comprising dissolving said mixture in deionized water.

35. The method recited in claim 32, further comprising dispensing chlorine dioxide from said mixture.

36. The method recited in claim 32, wherein said superabsorbent polymer comprises at least one of: a sodium salt of poly(acrylic acid), a potassium salt of poly(acrylic acid), straight poly(acrylic acid), poly(vinyl alcohol), polyacrylamide, and poly(chloro-trimethylaminoethyl acrylate).

37. The method recited in claim 32, wherein said aqueous chlorine dioxide solution is substantially entrapped in a solid matrix formed from said superabsorbent polymer.

38. The method recited in claim 32, wherein said mixture has said chlorine dioxide concentration of up to 5000 mg/L.

39. The method recited in claim 32, further comprising applying said liberated aqueous chlorine dioxide to a target.

40. The method recited in claim 32, further comprising disinfecting a target with said liberated aqueous chlorine dioxide.

41. The method recited in claim 32, further comprising disinfecting a target with said liberated aqueous chlorine dioxide, said target comprising at least one of water, wastewater, and a surface.

* * * * *